United States Patent [19]

Upsher

[11] Patent Number: 5,603,688

[45] Date of Patent: Feb. 18, 1997

[54] LARYNGOSCOPE INCLUDING AN UPWARDLY CURVED BLADE HAVING A DOWNWARDLY DIRECTED TIP PORTION

[75] Inventor: Michael S. Upsher, Menlo Park, Calif.

[73] Assignee: Upsher Laryngoscope Corporation, Foster City, Calif.

[21] Appl. No.: 427,416

[22] Filed: Apr. 24, 1995

[51] Int. Cl.⁶ ........................................... A61B 1/26
[52] U.S. Cl. .......................... 600/190; 600/185; 600/188; 600/199
[58] Field of Search .................................. 600/185, 188, 600/190, 193, 194, 199

[56] References Cited

U.S. PATENT DOCUMENTS

| | | | |
|---|---|---|---|
| 3,848,587 | 11/1974 | McDonald | 600/199 |
| 4,360,008 | 11/1982 | Corazzelli, Jr. | 600/194 |
| 4,384,570 | 5/1983 | Roberts | 600/185 |
| 4,527,553 | 7/1985 | Upsher | 600/188 |
| 4,567,882 | 2/1986 | Heller | 600/194 |
| 4,573,451 | 3/1986 | Bauman | 600/190 |
| 4,705,024 | 11/1987 | Bainton | 600/194 |

*Primary Examiner*—Richard J. Apley
*Assistant Examiner*—Beverly M. Flanagan
*Attorney, Agent, or Firm*—Stephen C. Shear

[57] ABSTRACT

An improved laryngoscope and its method of use are disclosed herein. The laryngoscope includes a handle and a blade wherein the blade includes a tip portion at its distal end which is positioned in a specific location relative to the rest of the blade when the blade and handle are positioned in their normal, operative downwardly directed position. In a method of using the laryngoscope as disclosed herein, the downwardly directed tip portion of the blade remains adjacent an endotracheal tube which follows a given path upon emerging at the distal end of the blade.

16 Claims, 2 Drawing Sheets

LARYNGOSCOPE INCLUDING AN UPWARDLY CURVED BLADE HAVING A DOWNWARDLY DIRECTED TIP PORTION

BACKGROUND OF THE INVENTION

The present invention relates generally to a laryngoscope, and more particularly to a laryngoscope including a blade which is upwardly curved and includes a downwardly directed tip portion for use in intubating a patient with a flexible endotracheal tube.

The use of a laryngoscope for the intubation of a patient, as well as its use in other procedures, is well known in the art. FIG. 1 illustrates one typical prior art laryngoscope, generally indicated by reference numeral 10. Laryngoscope 10 is shown in its normal operative downwardly directed position and includes a handle 12 extending upward (to be held by the operator) and an upwardly curved tubular blade 14 which are disengagably connectable with one another. Blade 14 includes a proximate end 16 and a distal end 18. Distal end 18 includes a tip portion 20 which forms the leading end of the blade. The blade also includes a tube passage (not shown) which extends from the proximate end to the distal end of the blade. The tube passage has an entrance opening 24 at the uppermost end of the blade and an exit opening 26 at the distal end of the blade. A light source (not shown) located in the handle provides light to a proximate end 28 of a fiber optic lighting member 30 carried by blade 14. Light received by fiber optic member 30 is transmitted to its distal end 32 to illuminate tip portion 20 of the blade and the anatomy of a patient (not shown) adjacent the tip portion when the laryngoscope is in actual use. A fiber optic viewing member 34 including an end 36 cooperates with the lighting member to provide for remote viewing at the tip portion using an eyepiece 38.

Still referring to FIG. 1, an endotracheal tube 40 is shown inserted through entrance 24 and on through the tube passage provided by the blade such that a leading end 40a of the tube extends outwardly from exit opening 26. The upward curvature of the blade near distal end 18 is specifically provided to best cooperate with the pharyngeal passage of a typical patient. This curvature, as illustrated, is generally approximately circular and is carried through tip portion 20 of the blade.

While the prior art laryngoscope, as depicted in FIGS. 1, is generally satisfactory for its intended purpose, there is a particular aspect of the instrument, as shown and described above, which may be improved upon in accordance with the present invention, as will be discussed below.

Referring once again to FIG. 1, it should be noted that endotracheal tube 40 is flexible in order to pass through the curved laryngoscope blade and in its relaxed state the tube maintains a radius of curvature which is greater than that of the distal end curve of the blade. Therefore, leading end 40a of the tube tends to follow a path upon emerging from tube passage 26 at the distal end of the blade which follows its own larger radius of curvature rather than the smaller curvature of the distal end. As a result, as leading end 40a emerges from distal end 18, it separates from tip portion 20 rather than hugging up against it, thereby defining an acute angle A therebetween. This downward curvature is caused in part by gravity along with the natural tendency of the somewhat resilient tube to want to bend back to its larger radius of curvature. A space 46 is thereby formed between the tube and adjacent tip 20 of the blade as defined by acute angle A. This separation at space 46 can lead to problems in an intubation procedure, which will be described immediately below.

A first problem resulting from the divergence or spacing between the tube and the tip portion occurs with regard to lighting member 30 and viewing member 34. Distal end 32 of the lighting member is fixedly attached to the blade and aimed to illuminate an area along tip portion 20. Similarly, end 36 of the viewing member is also fixedly aimed along the tip portion. In most cases, since the field of view through a fiber optic member is limited, leading end 40a of the tube will move out of the field of view of the viewing member or out of the area which is illuminated by the lighting member as the tube diverges from the tip portion in a downward direction. The benefit of the viewing member is thus lost at the critical point of the intubation procedure when it is desired to place the tube into the trachea.

If the spacing between leading end 40a of the tube and tip portion 20 is sufficiently great, in order to compensate for the spacing, the health care practitioner may have to manipulate the end of the blade in certain ways in order to properly align the tube with the patient's trachea.

As will be seen hereinafter, the present invention provides a solution for the problems caused by the emerging leading end of the tube diverging from the tip portion of the blade.

SUMMARY OF THE INVENTION

As will be described in more detail hereinafter, a laryngoscope for intubating a patient with a flexible endotracheal tube and method of using it are disclosed herein. This laryngoscope, like the prior art laryngoscope shown in FIG. 1, includes a handle and a blade disengagably connectable with the handle. The blade having a tube guiding portion with a proximate end adjacent the handle and a distal end further from the handle when the blade is connected therewith. At least a segment of the tube guiding portion including the distal end defines an upwardly curved path, when the blade and handle are disposed in their normal, operative downwardly directed position as is shown in FIG. 2. The tube guiding portion is configured to receive and route the flexible tube from its proximate end to the distal end along the curved path such that, upon emerging from the tube guiding portion at the distal end, the tube at least initially follows the same path described above with respect to FIG. 1. Unlike the prior art laryngoscope and in accordance with the present invention, the present blade, while still maintaining its upward curve which enables it to lift the epiglottis, includes a tip portion which extends forward from the distal end of the tube guiding portion in a direction immediately adjacent the tube as the latter emerges from the tube guiding portion, thereby eliminating the separation associated with the prior art arrangement described above.

In a method of intubating a patient with a flexible endotracheal tube using the laryngoscope of the present invention, in which the handle is disengagably connectable with the blade and the latter includes a tube guiding portion having a proximate end adjacent the handle and a curved segment including a distal end which is further from the handle, such that the curved segment defines a curved path, the method includes steps of: inserting the blade into the patient such that the blade curves upwardly, guiding the tube from the proximate end of the tube guiding portion to cause it to emerge therefrom at the distal end such that the tube at least initially follows a path away from the curved path, and providing a tip portion which extends forward from the distal end of the tube guiding portion in a direction immediately adjacent the tube as it emerges from the distal end of the blade and which also serves to elevate the patient's epiglottis while inserting the blade into the patient.

BRIEF DESCRIPTION OF THE DRAWINGS

The present invention may be understood by reference to the following detailed description taken in conjunction with the drawings, in which.

DETAILED DESCRIPTION OF THE INVENTION

Figure 1:
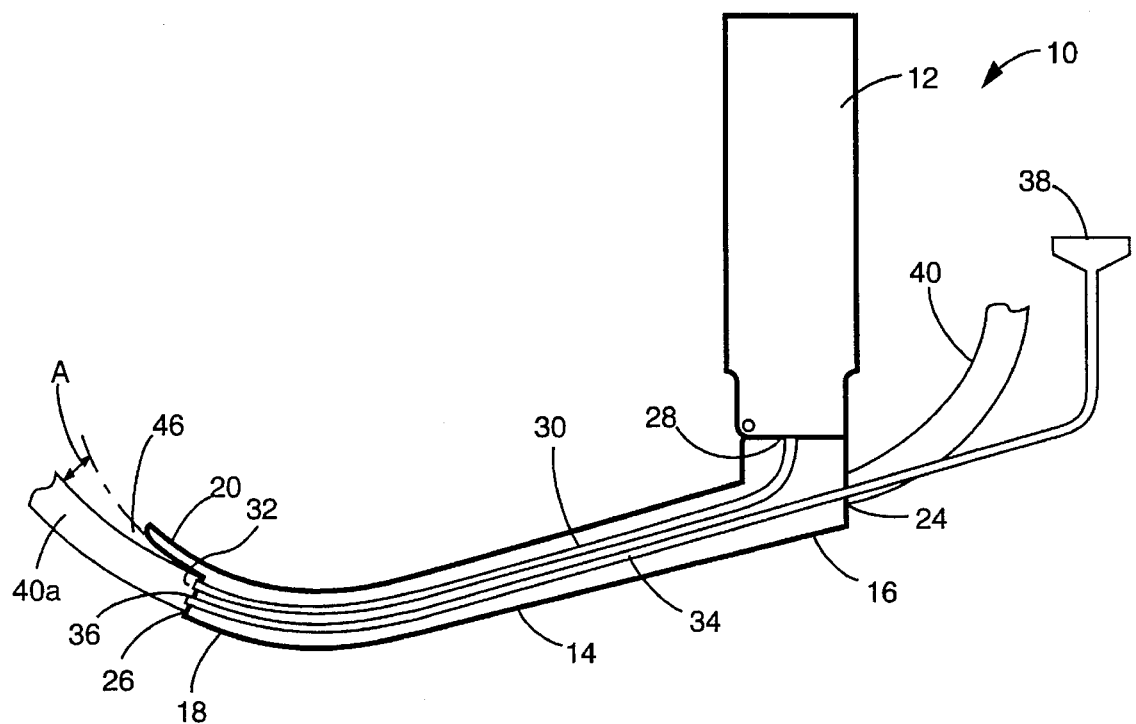
FIG. 1 illustrates a prior art laryngoscope which includes a prior art tip portion at the distal end of its blade.
Figure 2:
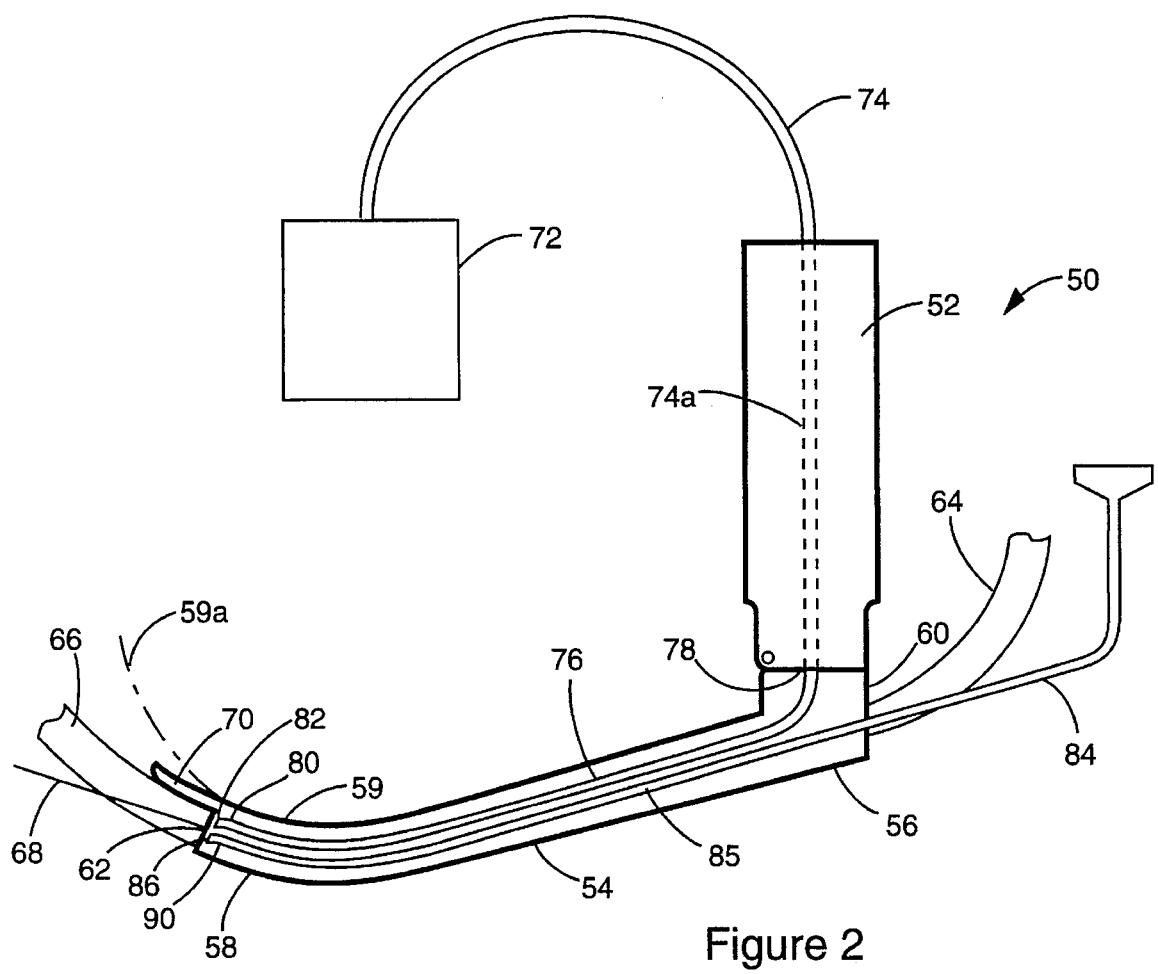
FIG. 2 is a side elevational view of a laryngoscope manufactured in accordance with the present invention including a downwardly directed tip portion.

Having described FIG. 1 previously, attention is immediately directed to FIG. 2 which illustrates a laryngoscope manufactured in accordance with the present invention and generally designated by reference numeral 50. Laryngoscope 50 is shown in its normal operative downwardly directed position and includes a handle 52 and an upwardly curved tubular blade 54 which is disengagably connectable with the handle, although the blade may be connected to the handle by any other suitable arrangement, such as unremovably fixing the handle to the blade. The laryngoscope of the present invention may incorporate any other feature of state of the art laryngoscopes such as, for example, a tube separation slot along a side margin of the blade. These features are not illustrated herein for simplicity.

Continuing to refer to FIG. 2, blade 54 also includes a proximate end 56 and a distal end 58. A segment 59 of the blade which includes distal end 58 defines a curved path, as shown, which path if extended along its radius would follow dotted line 59A in FIGS. 2 and 3. Segment 59 includes a circular curvature in the present example, but many variations in the curvature are possible within the scope of the invention and may be found to be useful. A tube guiding portion, which is not shown for simplicity, typical of prior art laryngoscopes, is formed by the tubular blade along its length and includes an entrance opening 60 at the proximate end of the blade and an exit opening 62 at the distal end of the blade. A flexible endotracheal tube 64 is shown inserted into the tube guiding portion such that a leading end 66 of the tube extends outwardly from exit opening 62. As discussed above in relation to the prior art laryngoscope, as leading end 66 of flexible tube 64 emerges from exit opening 62 along an initial path 68, it follows its own natural curvature which has a larger radius than the radius of curvature of segment 59 of the blade. The flexibility and behavior of the endotracheal tube, as just described, is typical of currently available endotracheal tubes.

In accordance with the present invention, a tip portion 70 integral with the distal end of the blade extends forward at an angle relative to the curved path defined by segment 59 of the tube guiding portion of the blade which directs the tip portion downward relative to the curved path in the direction of the emerging endotracheal tube in a manner such that the tip portion is immediately adjacent (touching or almost touching) the tube as it emerges from the blade along initial path 68. A variety of alternative configurations, other than the preferred embodiment described herein, for providing a tip portion are possible such as, for example, fixedly attaching a separate tip portion to the blade. Generally, the tip portion is configured to maintain its upward curvature but is bent downward at its most proximal portion and thus some curvature both along its length and cross-section may be found to be useful. The use of the laryngoscope including a tip portion which is immediately adjacent with the initial emerging path of the tube will be described hereinafter.

Still referring to FIG. 2, a remote light source 72, which is schematically illustrated, is connected to the handle by a fiber optic cable 74. Fiber optic cable 74 extends from the light source means to the handle and includes an end portion 74a which extends through the length of the handle. A light guide 76 extends along the length of the blade and includes a proximate end 78 which is disposed directly adjacent and opposite end portion 74a of the fiber optic cable when the blade is attached to the handle, as shown. When the remote light source is actuated, light is transmitted through cable 74 and is coupled to proximate end 78 of light guide 76, whereby to act as a source of light for the light guide. Remote light source 72 may be provided by a variety of light producing configurations, within the scope of the present invention. It is noted herein that an advantage is provided by the preferred embodiment described above, in that this configuration is capable of providing a light source which is typically much brighter than lighting means used with previous laryngoscopes.

Figure 3:
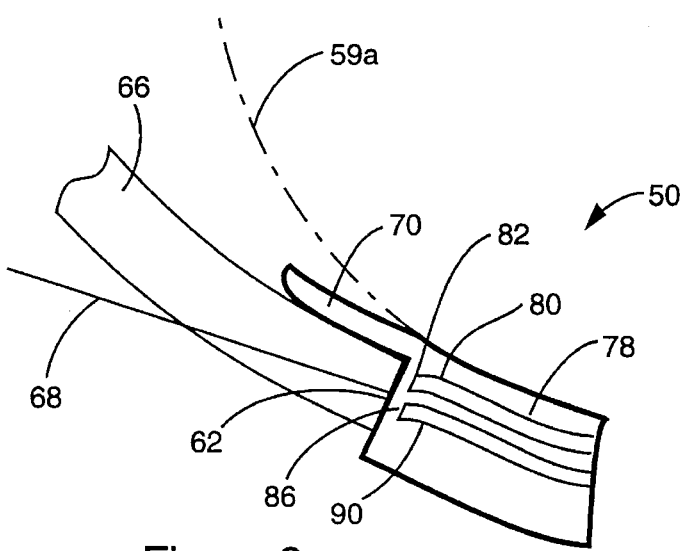
FIG. 3 is an enlarged elevational side view of the distal end of the blade of the laryngoscope which is shown in FIG. 2.

In accordance with the present invention and referring now to FIG. 3 in conjunction with FIG. 2, light guide 76 further includes an end segment 80 having an end face 82 at the distal end of the blade. Light originally incident upon proximate end 78 of the light guide is emitted from end face 82 to provide light along and directly forward of tip portion 70. The unique feature of this light guide resides in the disposition of end segment 80 on the blade. End segment 80 does not follow the general curvature of segment 59 of the blade but, rather, is aimed to project light from end face 80 along the tip portion in alignment with initial path 68 taken by the emerging endotracheal tube. Thus, in conjunction with the aimed end face of the lighting member, the projected light advantageously illuminates the tube and tip portion when the laryngoscope is oriented in its normal downward position in an operative procedure.

Many modifications may be made to the preferred embodiment, as described above, to provide light at the distal end of the blade. These may include, for example, incorporating the light source entirely within the handle, repositioning the light guide to an alternative margin on the blade or providing a second, additional light guide. All of these variations are considered to be within the scope of the invention provided only that the light is projected along the tip portion, as previously described.

Still referring to FIGS. 2 and 3, a flexible fiber optic viewing member 84 having a segment 85 attached to a side margin of the blade also includes a pickup end 86 to provide for remote viewing of the tip portion at an eyepiece 88 by transmitting reflected light which is incident on end 86 to the eyepiece. The eyepiece may also be adaptable for use with a video camera in which case the procedure may be observed on a video monitor. In accordance with the present invention, an end segment 90 at the distal end of viewing member 84 positions pickup end 86 of the viewing member so as to provide a view at eyepiece 88 which looks along tip portion 70 in general alignment with initial path 68. An advantageous view is thereby provided of the tip portion, the robe and the anatomy of the patient adjacent and directly ahead of the tip portion to ensure that leading end 66 of the tube remains in view throughout the duration of an intubation procedure. The appearance and location on the blade of the viewing member may be altered, but these changes are considered to be within the scope of the invention provided only that the viewing member looks along the tip portion, as described immediately above.

In use the laryngoscope blade is attached to the handle in its normal operative position, as shown in FIG. 2, and optical light source means 72 couples light to light guide 76 from end segment 74a of the fiber optic cable, as previously described. The blade is inserted into the throat of a patient (not shown) with segment 54a curving upwardly, as shown in FIG. 2. Tip portion 70 is used, as in prior art laryngoscopes, to elevate the epiglottis of the patient as the blade is inserted. In actual practice and as an unexpected benefit of the present invention, tip portion 70 has exhibited a general ease of use in being positioned under and elevating the epiglottis.

During the insertion of the blade, light emanates from the light guide to illuminate the throat area and the reflected light may be viewed through the viewing member. Once the blade is properly inserted in the pharynx and larynx, endotracheal tube 64 is guided through the tube guiding portion of the blade to emerge from exit opening 62. As described above, the tube, upon emerging at the distal end of the blade, will remain in close proximity to tip portion 70. Viewing member 84 now provides a direct view of the tube, the tip portion and larynx. The tube may now be inserted through the larynx and into the trachea while observing through the viewing member. It is emphasized here that the now adjacent relationship between the emerging tube and the tip portion, in cooperation with the end segments of the viewing and lighting members which are directed along the tip portion, provides a view of the tube as it enters the trachea, with the tube never leaving the field of view of the viewing member. In addition, since the tube does not diverge from the tip portion, an upward movement of the tip portion is not needed to initially place the tube into the trachea, to the benefit of the patient.

The laryngoscope of the present invention may be produced from a variety of materials, for example, such as stainless steel or suitable plastics which may even provide for disposability or a degree of flexibility in the blade. It is also anticipated herein that blades incorporating the features of the present invention may be provided which are adaptable for use with various prior art laryngoscope handles, which are currently in use, to provide the advantages herein disclosed.

Since a downwardly directed upwardly curved tip portion may be provided on the blade of a laryngoscope using a variety of configurations, it should be understood that the present invention may be embodied in many other specific forms without departing from the spirit or scope of the invention. Therefore, the present examples and methods are to be considered as illustrative and not restrictive, and the invention is not to be limited to the details given herein, but may be modified within the scope of the appended claims.

What is claimed is:

1. A laryngoscope for intubating a patient with a flexible endotracheal tube, said laryngoscope comprising:
   a) a handle; and
   b) a blade disengagably connectable with said handle, said blade including
      i. a tube guiding portion having a proximate end adjacent said handle when the blade is connected therewith and a distal end further from the handle when the blade is connected therewith, at least a segment of said tube guiding portion including said distal end defining an upwardly curved path, when the blade and handle are disposed in their normal, downwardly directed operating positions, said tube guiding portion being configured to receive and route said flexible tube from its proximate end to said distal end along said curved path such that, upon emerging from the tube guiding portion at the distal end, the tube at least initially follows a given path relative to said curved path, and
      ii. a tip portion extending forward from the distal end of said tube guiding portion and directed angularly downward relative to said curved path such that the tip portion is positioned immediately adjacent the initial given path of said tube as it emerges from said tube guiding portion, said tip portion serving to elevate the patient's epiglottis as the blade is inserted into the patient's throat.

2. A laryngoscope in accordance with claim 1 including means for directing light from said distal end of said blade in a direction generally parallel to the at least initial given path taken by said tube as it emerges from said tube guiding portion.

3. A laryngoscope in accordance with claim 2 wherein said light directing means includes a light guide on the blade and an optical light source means separate from the blade and the handle and in optical communication with said light guide when the blade is in the engaged position on the handle.

4. A laryngoscope in accordance with claim 2 including means for remotely viewing along said tip portion in a direction generally parallel to the at least initial given path taken by said tube as it emerges from said tube guiding portion.

5. A laryngoscope in accordance with claim 4 wherein said means for remotely viewing along said tip portion includes a viewing member positioned on the blade, said viewing member including an end segment positioned at the distal end of the blade generally parallel with said at least initial given path and not contained by said curved path for providing a remote view of the tip portion and the surrounding anatomy of said patient.

6. A laryngoscope in accordance with claim 2 wherein said light directing means includes a light guide on the blade, said light guide including an end segment positioned at the distal end of the blade generally parallel with said at least initial given path and not contained by said curved path for emitting light which illuminates the tip portion and the surrounding anatomy of said patient.

7. A laryngoscope for intubating a patient with a flexible endotracheal tube, said laryngoscope comprising:
   a) a handle; and
   b) a blade disengagably connectable with said handle, said blade including
      i. a tube guiding portion having a proximate end adjacent said handle when the blade is connected therewith and a distal end further from the handle when the blade is connected therewith, at least a segment of said tube guiding portion including said distal end defining an upwardly curved path, when the blade and handle are disposed in their normal, downwardly directed operating positions, said tube guiding portion being configured to receive and route said flexible tube from its proximate end to said distal end along said curved path such that, upon emerging from the tube guiding portion at the distal end, the tube at least initially follows a given path relative to said curved path, ii. a tip portion extending forward from the distal end of said tube guiding portion and directed angularly downward relative to said curved path such that the tip portion is positioned generally parallel with said initial downward path of said tube as it emerges from said tube guiding portion, said tip portion serving to elevate the patient's epiglottis as the blade is inserted into the patient's throat, iii. a light guide attached to the blade and including opposing first and second ends wherein said first end is positioned for directing light from said distal end of said blade in a direction generally parallel to the at least initial given path taken by said tube as it emerges from said tube guiding portion, iv. optical light source means in optical communication with said second end of the light guide for providing light to the latter when the blade is in the engaged position on the handle, and v. means for remotely viewing along said tip portion in a direction generally parallel to the at least initial path taken by said tube as it emerges from said tube guiding portion.

8. A method of intubating a patient with a flexible endotracheal tube using a laryngoscope including a handle and a blade disengagably connectable with said handle, said blade including a tube guiding portion having a proximate end engaging the handle and a distal end such that at least a segment of said tube guiding portion including said distal end defines a curved path, said method including the steps of:

a) inserting the blade into said patient such that the blade curves upwardly;

b) guiding said tube from said proximate end through said tube guiding portion to cause it to emerge from the tube guiding portion at the distal end such that the tube at least initially follows a given path relative to said curved path;

c) providing a tip portion extending forward from the distal end of the tube guiding portion and directed angularly downward relative to said curved path such that the tip portion is positioned immediately adjacent said initial given path;

d) while inserting the blade into the patient, elevating the patient's epiglottis using said tip portion; and e) placing the tube in position in the patient's trachea.

9. A method according to claim 8 including the step of directing light from said tip portion in a direction generally parallel to said initial given path.

10. A method according to claim 9 including the step of remotely viewing along said tip portion in a direction generally parallel to said initial given path.

11. A blade for use in intubating a patient with a flexible endotracheal tube as part of a laryngoscope which also includes a handle which is disengagably connectable with the blade, said blade comprising:

a) a tube guiding portion having a proximate end adjacent said handle when the blade is connected therewith and a distal end further from the handle when the blade is connected therewith, at least a segment of said tube guiding portion including said distal end defining an upwardly curved path, when the blade and handle are disposed in their normal, downwardly directed operating positions, said tube guiding portion being configured to receive and route said flexible tube from its proximate end to said distal end along said curved path such that, upon emerging from the tube guiding portion at the distal end, the tube at least initially follows a given path relative to said curved path, and b) a tip portion extending forward from the distal end of said tube guiding portion and directed angularly downward relative to said curved path such that the tip portion is positioned immediately adjacent the initial given path of said tube as it emerges from said tube guiding portion, said tip portion serving to elevate the patient's epiglottis as the blade is inserted into the patient's throat.

12. A blade in accordance with claim 11 including means for directing light from said distal end of said blade in a direction generally parallel to the at least initial given path taken by said tube as it emerges from said tube guiding portion.

13. A blade in accordance with claim 12 wherein said light directing means includes a light guide on the blade and an optical light source means in optical communication with said light guide when the blade is in the engaged position on the handle.

14. A blade in accordance with claim 12 including means for remotely viewing along said tip portion in a direction generally parallel to the at least initial given path taken by said tube as it emerges from said tube guiding portion.

15. A blade in accordance with claim 14 wherein said means for remotely viewing along said tip portion includes a viewing member positioned on the blade, said viewing member including an end segment positioned at the distal end of the blade generally parallel with said at least initial given path and not contained by said curved path for providing a remote view of the tip portion and the surrounding anatomy of said patient.

16. A blade in accordance with claim 12 wherein said light directing means includes a light guide on the blade, said light guide including an end segment positioned at the distal end of the blade generally parallel with said at least initial given path and not contained by said curved path for emitting light which illuminates the tip portion and the surrounding anatomy of said patient.

* * * * *